United States Patent
Pflanz et al.

(10) Patent No.: US 11,911,741 B2
(45) Date of Patent: Feb. 27, 2024

(54) DIATOMACEOUS EARTH COMPOSITION WITH A LOW ENDOTOXIN CONTENT

(71) Applicant: Sartorius Stedim Biotech GMBH, Göttingen (DE)

(72) Inventors: Karl Pflanz, Gleichen (DE); Florian Hebenstreit, Beberstedt (DE); Andreas Pickl, Klein Schneed (DE)

(73) Assignee: Sartorius Stedim Biotech GMBH, Gottingen (DE)

( * ) Notice: Subject to any disclaimer, the term of this patent is extended or adjusted under 35 U.S.C. 154(b) by 986 days.

(21) Appl. No.: 16/648,521

(22) PCT Filed: Oct. 9, 2018

(86) PCT No.: PCT/EP2018/077456
§ 371 (c)(1),
(2) Date: Mar. 18, 2020

(87) PCT Pub. No.: WO2019/076683
PCT Pub. Date: Apr. 25, 2019

(65) Prior Publication Data
US 2020/0261883 A1    Aug. 20, 2020

(30) Foreign Application Priority Data
Oct. 17, 2017   (EP) .................................... 17001714

(51) Int. Cl.
| | |
|---|---|
| *B01J 20/14* | (2006.01) |
| *B01J 20/30* | (2006.01) |
| *B01J 20/28* | (2006.01) |
| *B01D 37/02* | (2006.01) |
| *A61L 2/08* | (2006.01) |
| *C12M 1/00* | (2006.01) |
| *B65D 65/40* | (2006.01) |
| *B65B 55/02* | (2006.01) |

(52) U.S. Cl.
CPC ............... *B01J 20/14* (2013.01); *A61L 2/081* (2013.01); *B01D 37/02* (2013.01); *B01J 20/28004* (2013.01); *B01J 20/2805* (2013.01); *B01J 20/28016* (2013.01); *B01J 20/3028* (2013.01); *B65B 55/02* (2013.01); *B65D 65/40* (2013.01); *C12M 47/02* (2013.01); *C12M 47/10* (2013.01); *A61L 2202/21* (2013.01)

(58) Field of Classification Search
CPC   B01J 20/14; B01J 20/28004; B01J 20/28016; B01J 20/2805; B01J 20/3028; A61L 2/081; B01D 37/02; B65B 55/02; B65D 65/40; C12M 47/02; C12M 47/10
See application file for complete search history.

(56) References Cited

U.S. PATENT DOCUMENTS 5,576,196 A  *  11/1996  Horn .................. C12N 15/1017
                                                    435/6.12
2004/0105778 A1     6/2004  Lee et al.

FOREIGN PATENT DOCUMENTS

| AU | 2147683 A | 3/1984 | |
| AU | 542983 B2 | 3/1985 | |
| JP | H10118426 A * | 5/1998 | ............. B01D 37/02 |
| JP | H10118426 A | 5/1998 | |

OTHER PUBLICATIONS

Celite®—Product-Brochure_copyright 1999.*
Sartorius; Validation Guide; Diatomaceous Earth—Celpure C300; 8-pages.
Van Der Meer et al., Diatomaceous Earth Filtration; Innovative Single-Use Concepts for Clarification of Hight-Density Mammalian Cell Cultures; BioProcess; 4-pages.

* cited by examiner

*Primary Examiner* — Yong L Chu
(74) *Attorney, Agent, or Firm* — Stinson LLP

(57) ABSTRACT

The present invention relates to a diatomaceous earth composition with a low endotoxin content, comprising an agglomerated mixture of calcined diatomaceous earth particles and water, wherein the mass ratio of calcined diatomaceous earth particles and water is in the range of 1:1.0 to 1:2.0, and wherein the endotoxin content of the diatomaceous earth composition is equal to or less than 0.5 EU/mL. In a further aspect, the present invention relates to a method for producing the diatomaceous earth composition with a low endotoxin content. In another aspect, the present invention relates to the use of the diatomaceous earth composition with a low endotoxin content as a precoat agent for the precoat filtration in biopharmaceutical applications.

7 Claims, 2 Drawing Sheets

DIATOMACEOUS EARTH COMPOSITION WITH A LOW ENDOTOXIN CONTENT

This application claims priority to International Application No. PCT/EP2018/077456, filed on Oct. 9, 2018, which claims priority to European Patent Application No. 17001714.9, filed on Oct. 17, 2017, each of which is hereby incorporated by reference herein in its entirety.

The present invention relates to a diatomaceous earth composition with a low endotoxin content. In a further aspect, the present invention relates to a method for producing the diatomaceous earth composition with a low endotoxin content. In another aspect, the present invention relates to the use of the diatomaceous earth composition with a low endotoxin content as a precoat agent for the precoat filtration in biopharmaceutical applications.

In the biopharmaceutical process, cells which produce a product such as antibodies are usually propagated in fermenters. At the end of the fermentation process, the cells as well as the cell debris have to be separated from the product in order to obtain a clear supernatant with the desired product.

Typically, in order to achieve this separation, centrifugation is performed with subsequent sterile filtration. However, sterile filtration frequently results in blocking of the filter after a certain time, which makes the use of several filters inevitable for the processing of a fermenter. Sterile filtration without prior centrifugation would immediately lead to a blockage of the filter, thereby even making filtration impossible. The entire separation procedure, including centrifugation and sterile filtration, requires a significantly long time and is connected to complicated working steps and thus increased costs.

One way in which the centrifugation step and the blocking of the filter can be circumvented is precoat filtration using diatomaceous earth (DE). For this purpose, diatomaceous earth is added in a certain amount to the cell broth and then filtered. During this precoat filtration, diatomaceous earth builds a coarse-pore filter cake on the sterile filter in which the cells and the cell debris are bound, which can thus no longer contribute to the blockage of the filter.

In brief, diatomaceous earth is a naturally occurring, soft, siliceous sedimentary rock which is composed of the fossilized remains of diatoms, a type of hard-shelled protists, also referred to as chrysophytes. From a chemical perspective, diatomaceous earth is mostly composed of amorphous silica, but also contains a considerable amount of crystalline silica. Depending on its natural deposit and on its further processing such as calcination, diatomaceous earth may contain up to 15 mass % cristobalite and 1 mass % quartz.

For the use of diatomaceous earth in laboratories, the open dosage, e.g. via a funnel, is preferred, since various fermenter shapes and typically multiple samples have to be complied with. On an industrial scale, specifically developed packaging solutions can be used which allow for a mostly dust-free connectivity.

A major problem arising from the application of diatomaceous earth in the laboratory is the extremely high release of dust particles, which particularly occurs when using the dry material which has a powdery morphology. As a result, diatomaceous earth in its pure form is not suitable for working outside of safety workbenches supplied with fume hoods. In particular, due to the considerable amount of crystalline silica in terms of cristobalite and quartz, both of which are highly respirable, the inhalation of dust particles released from diatomaceous earth is harmful to the lungs, causing silicosis. Moreover, crystalline silica has also been presumed to be a carcinogen for humans. In contrast thereto, amorphous silica is considered to have a low toxicity. Nevertheless, the prolonged inhalation thereof may lead to an alteration of the lungs. In addition to the above considerations in view of health issues, the generation of dust results in further problems regarding general hygienic requirements in the working environment.

Attempts to form granulates of diatomaceous earth by using binders do not significantly reduce the release of dust particles, since such granulates also generate dust particles by friction, which are then released when handled in an open manner. Besides, a disadvantage of this approach lies in the binders as such, which are introduced into the sample solution, thereby contaminating the sample and possibly interfering with the subsequent analysis thereof.

Moistening of diatomaceous earth with water reduces the release of dust particles. Furthermore, it allows for an open handling and does not add any new substances to the aqueous sample. Depending on the mass ratio of diatomaceous earth and water, products from crumbly to solid shape are obtained. However, these products are often difficult to handle, since they are no longer free-flowing, in particular when the mass ratio is about 1:3 or even less. Besides, adding large amounts of water to the diatomaceous earth leads to a further undesirable dilution of the sample. A further problem which results from the additional input of water is the promotion of germ growth and the endotoxin formation associated therewith, leading to a contamination of the sample.

In view of the above disadvantages, the technical problem underlying the present invention is to provide a diatomaceous earth composition which shall exhibit a significantly reduced release of dust particles and at the same time a low endotoxin content. In particular, the diatomaceous earth composition to be provided shall allow for an almost dust-free application in precoat filtration. Furthermore, it is an object of the present invention to provide a method for producing said diatomaceous earth composition.

The above problems are solved by providing the embodiments characterized in the claims.

In particular, according to a first aspect of the present invention, there is provided a diatomaceous earth composition with a low endotoxin content, comprising an agglomerated mixture of calcined diatomaceous earth particles and water, wherein the mass ratio of calcined diatomaceous earth particles and water is in the range of 1:1.0 to 1:2.0, and wherein the endotoxin content of the diatomaceous earth composition is equal to or less than 0.5 EU/mL.

Due to the optimized mass ratio of calcined diatomaceous earth particles and water, the diatomaceous earth composition according to the present invention exhibits a particularly low release of dust particles. In particular, when compared to dry diatomaceous earth, the diatomaceous earth composition according to the present invention allows to reduce the amount of released dust particles by more than 80% (cf. FIG. 1). As such, it can be handled in an open manner without significant health risks.

Furthermore, the diatomaceous earth composition according to the present invention has a low endotoxin content, thus being particularly suitable for biopharmaceutical applications, e.g. for the precoat filtration of eukaryotic and prokaryotic cells, where the absence of endotoxins is highly desired.

As mentioned above, the diatomaceous earth composition according to the present invention comprises an agglomerated mixture of calcined diatomaceous earth particles and water.

Herein, the diatomaceous earth particles used may be calcined by any method known in the art. Due to the calcination, the diatomaceous earth particles are free of water. Thereby, it is possible to precisely adjust the mass ratio of calcined diatomaceous earth particles and water, since no additional amount of water is added by the calcined diatomaceous earth particles.

In addition, the calcined diatomaceous earth particles are preferably substantially free of organic residues originating from their algae origin. For this purpose, the diatomaceous earth particles may undergo extensive (acidic) washing procedures before and/or after calcination.

Preferably, the water used for the above-defined diatomaceous earth composition is free of endotoxins and free of bacteria, with the latter to be regarded as the source of endotoxins. Thereby, it is possible to easily ensure a low endotoxin content in the diatomaceous earth composition according to the present invention. Water which is free of endotoxins and free of bacteria can be obtained by γ-sterilization, for instance, as described further below in more detail.

Wherever applicable in the present application, the term "free of" is not deemed to be construed literally, i.e. it shall rather mean "substantially free of". Accordingly, a tiny amount may be encompassed by the term "free of" as long as it does not adversely affect the advantageous effects of the present invention.

According to the present invention, the mass ratio of calcined diatomaceous earth particles and water is in the range of 1:1.0 to 1:2.0. Accordingly, by mixing the calcined diatomaceous earth particles and water in the above-mentioned mass ratio, agglomerates are formed which contain the calcined diatomaceous earth particles in an amount of 33.3 to 50.0 mass %, and which contain water in an amount of 50.0 to 66.7 mass %.

In a preferred embodiment of the above-defined diatomaceous earth composition, the mass ratio of calcined diatomaceous earth particles and water is in the range of 1:1.1 to 1:1.7. That is, in this preferred embodiment, the agglomerates formed contain the calcined diatomaceous earth particles in an amount of 37.0 to 47.6 mass %, and contain water in an amount of 52.4 to 63.0 mass %.

In a more preferred embodiment of the diatomaceous earth composition as defined above, the mass ratio of calcined diatomaceous earth particles and water is in the range of 1:1.2 to 1:1.4. That is, in this more preferred embodiment, the agglomerates formed contain the calcined diatomaceous earth particles in an amount of 41.7 to 45.5 mass %, and contain water in an amount of 54.5 to 58.3 mass %.

In case the mass ratio of calcined diatomaceous earth particles and water falls within the ranges as defined above, the diatomaceous earth composition according to the present invention, which comprises the calcined diatomaceous earth particles and water in form of an agglomerated mixture, exhibits a particularly low release of dust particles.

As far as the average particle size of the calcined diatomaceous earth particles is concerned, the present invention is not particularly limited. For example, the average particle size may be in the range of 0.1 to 800 µm, e.g. 0.1 to 600 µm, 0.1 to 400 µm, 0.1 to 200 µm or 0.2 to 200 µm, without being limited thereto. In a specific embodiment of the above-defined diatomaceous earth composition, the average particle size of the calcined diatomaceous earth particles is in the range of 0.5 to 10 µm. For adjusting the average particle size, the diatomaceous earth particles as obtained after the calcination may be classified using any mechanical separation procedure known in the art. In case the average particle size of the calcined diatomaceous earth particles falls within the above-defined ranges, an agglomerated mixture can be obtained, wherein the calcined diatomaceous earth particles are sufficiently free-flowing. Herein, the average particle size of the calcined diatomaceous earth particles is measured by laser diffraction (accuracy: ±1%), using a conventional particle sizing instrument (Mastersizer 2000, Malvern Instruments).

In another specific embodiment of the present invention, the diatomaceous earth composition as defined above further comprises a water-impermeable and γ-sterilizable packaging which seals the agglomerated mixture of calcined diatomaceous earth particles and water, i.e. which encloses the agglomerated mixture in a hermetic manner so that practically no material exchange with the environment can take place.

Due to the water-impermeability of the packaging, it can be ensured that the mass ratio of calcined diatomaceous earth particles and water is maintained during storage of the above-defined diatomaceous earth composition even over a longer period of time, such as several months up to three years. That is, the diatomaceous earth composition when being packaged is prevented from readily turning back into the dry form which is prone to release dust particles. Advantageously, in case the above-defined diatomaceous earth composition is packaged, it can be easily stored in different quantities and shipped. After removal of the packaging, the desired quantity can be dosed in an almost dust-free manner.

Furthermore, since the packaging is γ-sterilizable, i.e. the packaging itself as well as the content thereof can be sterilized through irradiation with γ-rays, it is possible to obtain an endotoxin content of equal to or less than 0.5 EU/mL in the diatomaceous earth composition according to the present invention, as described further below.

From a chemical perspective, endotoxins are lipopolysaccharides. They are components of gram-negative bacterial cell walls, which are known to induce fever in humans, e.g. when injected into the bloodstream. The presence of endotoxins in the blood, which is also referred to as endotoxemia, leads to septic shocks if the immune response is severely pronounced. Disadvantageously, bacterial endotoxins are heat-stable, and their toxicity is not dependent on the presence of bacterial cells.

Herein, the endotoxin content of the diatomaceous earth composition is measured in accordance with the limulous amoebocyte lysate test, simply abbreviated as LAL test, which is the most common method known in the art for endotoxin testing. In brief, the assay which underlies the LAL test is based on the biology of the horseshoe crab (Limulous) which produces LAL enzymes in blood cells (amoebocytes) to bind and inactivate the endotoxin from invading bacteria. Specifically, LAL serves as a primitive immune system. By inactivating the endotoxin, a clot is formed, which can further protect the horseshoe crab from infection. The LAL test exploits the action of this enzyme, by adding LAL reagent to the sample to be tested, and assaying for clot formation. This can be achieved by optical means as the clot formation renders the sample cloudy. The endotoxin content is specified in terms of a concentration in "endotoxin units" (EU) per volume, e.g. in EU/mL, which approximately corresponds to 0.1 to 0.2 ng endotoxin per milliliter of the sample volume.

As known to the skilled person, endotoxin contents can be also measured using the recombinant Factor C (rFC)-based endotoxin test, which has been approved as an alternative to the conventional LAL test as described above, whilst sparing the endangered horseshoe crabs. The recombinant Factor C-based endotoxin test is endotoxin specific and can eliminate false-positive glucan reactions. Specifically, in the recombinant Factor C-based endotoxin test, the synthetic form of Factor C binds to endotoxins, thereby activating a clotting cascade. Typical rFC-based assays are end-point fluorescence tests, wherein the non-bound Factor C cleaves a fluorogenic substrate, thereby releasing a detectable fluorescent substance.

Herein, the endotoxin content of the diatomaceous earth composition according to the present invention is measured in accordance with the above-described LAL test.

According to the present invention, the endotoxin content of the diatomaceous earth composition as defined above is equal to or less than 0.5 EU/mL, preferably equal to or less than 0.2 EU/mL, and more preferably equal to or less than 0.1 EU/mL. Generally, the lower limit of the endotoxin content is not particularly limited according to the present invention. For example, the lower limit may correspond to the lower detection limit of the LAL test, which is about 0.01 EU/mL. Accordingly, a sample having an endotoxin content of 0.01 EU/mL may be considered as being free of endotoxins.

For measuring the endotoxin content, the diatomaceous earth composition according to the present invention is dissolved in 1 L water. Herein, the amount of the diatomaceous earth composition to be dissolved in 1 L water is always such that 40 g of the calcined diatomaceous earth particles are included in the finally obtained solution. For example, in case the mass ratio of the calcined diatomaceous earth particles and water is 1:1.0 in the diatomaceous earth composition, 80 g thereof are dissolved in 1 L water. In line with this, in case the mass ratio of the calcined diatomaceous earth particles and water is 1:2.0 in the diatomaceous earth composition, 120 g thereof are dissolved in 1 L water. In any case, the endotoxin content according to the present invention, measured with the LAL test as described above, is equal to or less than 0.5 EU/mL, preferably equal to or less than 0.2 EU/mL, and more preferably equal to or less than 0.1 EU/mL, based on the volume of the finally obtained solution, approximately corresponding to an endotoxin content of equal to or less than 12.5 EU/g, preferably equal to or less than 5 EU/g, and more preferably equal to or less than 2.5 EU/g, based on the mass of the calcined diatomaceous earth particles, respectively.

In case the diatomaceous earth composition according to the present invention is packaged, the packaging used for sealing the diatomaceous earth composition, which may be a bag or a container, for instance, is not particularly limited as long as it is water-impermeable, in particular impermeable to water vapor, and γ-sterilizable. Typically, laminates composed of different polymeric and metallic layers may be used as the material for the packaging.

In a specific embodiment of the diatomaceous earth composition as defined above, the water-impermeable and γ-sterilizable packaging is composed of a four-layered laminate comprising the following layers (i) to (iv) from the inside to the outside of the packaging, i.e. from the contact side to the agglomerated mixture of calcined diatomaceous earth particles and water towards the surrounding environment:
  (i) a layer of polyethylene (PE) or polypropylene (PP) having a thickness in the range of 30 to 150 μm, preferably in the range of 50 to 120 μm, e.g. 75 μm or 100 μm;
  (ii) a layer of polyethylene terephthalate (PET) or oriented polyamide (OPA) having a thickness in the range of 5 to 20 μm, preferably in the range of 8 to 15 μm, e.g. 12 μm;
  (iii) a layer of aluminum (ALU) having a thickness in the range of 5 to 20 μm, preferably in the range of 8 to 15 μm, e.g. 12 μm; and
  (iv) a layer of polyethylene terephthalate (PET) having a thickness in the range of 5 to 20 μm, preferably in the range of 8 to 15 μm, e.g. 12 μm.

In the above-defined four-layered laminate, PE or PP on the inside of the packaging is used as a material for a retort-stable heat sealing layer. The thickness of the PE or PP layer mainly influences the mechanical strength, sealing strength and stiffness of the laminate, being essential for ensuring tight seals. The intermediate PET or OPA layer provides mechanical strength, e.g. puncture resistance and drop resistance, as well as sealing strength, thereby protecting the bond to the ALU layer which is the barrier layer. That is, aluminum is used as a barrier material mainly against oxygen, light and water. Due to the presence of the ALU layer, the four layered-laminate as defined above has a water permeability of at most 0.05 g/m²·day, e.g. at most 0.03 g/m²·day or at most 0.02 g/m²·day, and thus can be considered water-impermeable in the sense of the present invention. Finally, the PET layer on the outside acts as a protecting layer, provides stiffness and tensile strength, and serves as a sealing-resistant substrate for printing of the packaging, as required. Generally, the thicknesses of the four layers (i) to (iv) may be appropriately set with respect to the pouch size, the filling machine, and the mechanical strength and stiffness requirements.

Typical combinations of the above-defined four layers (i) to (iv), which are excellent in water-impermeability, in particular excellent in permeability to water vapor, include PE (100 μm)/PET (12 μm)/ALU (12 μm)/PET (12 μm) as well as PE (75 μm)/OPA (12 μm)/ALU (12 μm)/PET (12 μm), without being limited thereto. The above-mentioned four-layered laminates can be readily exposed to γ-radiation without being damaged, thus allowing for the γ-sterilization of the packaging which seals the agglomerated mixture of calcined diatomaceous earth particles and water.

In a further aspect, the present invention relates to a method which allows to produce the above-defined diatomaceous earth composition. In this respect, all limitations and definitions provided above for the diatomaceous earth composition according to the present invention equally apply to the method for producing a diatomaceous earth composition according to the present invention, and vice versa.

In particular, the method for producing a diatomaceous earth composition according to the present invention comprises the following steps (a) to (e):
  (a) providing calcined diatomaceous earth particles;
  (b) mixing the calcined diatomaceous earth particles with water in a mass ratio of 1:1.0 to 1:2.0, thereby obtaining an agglomerated mixture of calcined diatomaceous earth particles and water;
  (c) sealing the agglomerated mixture of calcined diatomaceous earth particles and water obtained in step (b) in a water-impermeable and γ-sterilizable packaging, thereby obtaining a sealed agglomerated mixture of calcined diatomaceous earth particles and water;
  (d) sterilizing the sealed agglomerated mixture of calcined diatomaceous earth particles and water obtained in step (c) by exposure to γ-radiation, thereby obtaining a diatomaceous earth composition with an endotoxin content of equal to or less than 0.5 EU/mL; and
(e) optionally removing the packaging from the diatomaceous earth composition obtained in step (d).

Hereinafter, steps (a) to (e) of the method for producing a diatomaceous earth composition according to the present invention are described in more detail.

In step (a) of the method as defined above, calcined diatomaceous earth particles are provided. As mentioned above, the diatomaceous earth particles which are provided in step (a) have been subjected to calcination in advance so as to ensure that they are free of water, thereby allowing for a precise adjustment of the mass ratio to be adjusted in the following step (b).

In step (b) of the method as defined above, the calcined diatomaceous earth particles are mixed with water, wherein the mass ratio of calcined diatomaceous earth particles and water is in the range of 1:1.0 to 1:2.0, preferably in the range of 1:1.1 to 1:1.7, and more preferably in the range of 1:1.2 to 1:1.4. Thereby, an agglomerated mixture of calcined diatomaceous earth particles and water is obtained. Upon mixing, the obtained agglomerates contain the calcined diatomaceous earth particles in an amount of 33.3 to 50.0 mass %, preferably in an amount of 37.0 to 47.6 mass %, and more preferably in an amount of 41.7 to 45.5 mass %, while containing water in an amount of 50.0 to 66.7 mass %, preferably in an amount of 52.4 to 63.0 mass %, and more preferably in an amount of 54.5 to 58.3 mass %. As far as the water used in step (b) to produce the desired agglomerates is concerned, it is preferred that it is free of endotoxins and free of bacteria so as to facilitate the γ-sterilization to be conducted in step (d).

As far as the average particle size of the calcined diatomaceous earth particles is concerned, the above-defined method is not particularly limited. As mentioned in connection with the diatomaceous earth composition according to the present invention, the average particle size may be in the range of 0.1 to 800 μm, e.g. 0.1 to 200 μm or 0.2 to 200 μm, without being limited thereto. In a specific embodiment of the above-defined method, the average particle size of the calcined diatomaceous earth particles provided in step (a) is in the range of 0.5 to 10 μm. In case the above-defined ranges for the average particle size are met, the diatomaceous earth composition obtainable by the above-defined method is sufficiently free-flowing.

Herein, the mixing of the calcined diatomaceous earth particles and water can be conducted by any mixing technique known in the art. In a specific embodiment of the above-defined method, the calcined diatomaceous earth particles and water are mixed by spray-wetting in step (b). Typically, spray wetting comprises fluidizing the calcined diatomaceous earth particles, and spraying water thereonto during the fluidization, resulting in the formation of agglomerates until the desired mass ratio of calcined diatomaceous earth particles and water is achieved. Alternatively, the calcined diatomaceous earth particles and water can be mixed in a conventional mixing machine, e.g. a ploughshare mixer, while stirring. For this purpose, it is preferable to fill the calcined diatomaceous earth particles into the mixing machine before water is added.

In order to prevent the contamination with bacteria, which might lead to the formation of endotoxins, the agglomerated mixture of calcined diatomaceous earth particles and water obtained in step (b) of the above-defined method may be cooled, e.g. at a temperature of 0° C. to 15° C., 0° C. to 10° C., or 5° C. to 10° C., as required, before carrying out step (c).

In step (c) of the method as defined above, the agglomerated mixture of calcined diatomaceous earth particles and water which has been obtained in step (b) is sealed in a water-impermeable and γ-sterilizable packaging. Thereby, a sealed agglomerated mixture of calcined diatomaceous earth particles and water is obtained. Prior to the sealing, the agglomerated mixture obtained in step (b) is transferred into the packaging, which is e.g. a bag or a container, by any means known in the art, typically at room temperature (25° C.). Then, the sealing may be achieved by application of heat, which is also referred to as thermal sealing. However, the present invention is not limited to any specific sealing procedure.

As mentioned above, the packaging is not particularly limited as long as it is water-impermeable, in particular impermeable to water vapor, as well as γ-sterilizable. Furthermore, the packaging provided for sealing the agglomerated mixture of calcined diatomaceous earth particles and water in step (c) may be for single use or for multiple use, i.e. it may be re-sealable or not.

In a specific embodiment of the above-defined method, the water-impermeable and γ-sterilizable packaging for sealing the agglomerated mixture of calcined diatomaceous earth particles and water in step (c) is composed of a four-layered laminate comprising the following layers (i) to (iv) from the inside to the outside of the packaging:
(i) a layer of polyethylene (PE) or polypropylene (PP) having a thickness in the range of 30 to 150 μm, preferably in the range of 50 to 120 μm, e.g. 75 μm or 100 μm;
(ii) a layer of polyethylene terephthalate (PET) or oriented polyamide (OPA) having a thickness in the range of 5 to 20 μm, preferably in the range of 8 to 15 μm, e.g. 12 μm;
(iii) a layer of aluminum (ALU) having a thickness in the range of 5 to 20 μm, preferably in the range of 8 to 15 μm, e.g. 12 μm; and
(iv) a layer of polyethylene terephthalate (PET) having a thickness in the range of 5 to 20 μm, preferably in the range of 8 to 15 μm, e.g. 12 μm.

For the sake of conciseness, reference is made to the text passages hereinabove, where the water-impermeable and γ-sterilizable packaging for sealing the agglomerated mixture of calcined diatomaceous earth particles and water has been described in detail.

The sealed agglomerated mixture of calcined diatomaceous earth particles and water obtained in step (c) of the above-defined method may be cooled in the same manner as explained above in connection with step (b). Thereby, it can be ensured that the sealed agglomerated mixture is not further contaminated with bacteria, which might lead to the formation of endotoxins.

In step (d) of the method as defined above, the sealed agglomerated mixture of calcined diatomaceous earth particles and water which has been obtained in step (c) is sterilized by exposure to γ-radiation. Thereby, a diatomaceous earth composition with an endotoxin content of equal to or less than 0.5 EU/mL is obtained.

As known to the skilled person, sterilization of a sample by exposure to γ-radiation is a powerful tool for removing germs, such as bacteria. Since endotoxins are released upon disintegration of gram-negative bacteria, the removal of such bacteria ensures a low endotoxin content in the sterilized sample.

In a specific embodiment of the above-defined method, the dose of the γ-radiation for sterilizing the sealed agglomerated mixture of calcined diatomaceous earth particles and water in step (d) is in the range of 25 to 100 kGy, e.g. 40 to 80 kGy, 50 to 70 kGy, for example at least 25 kGy, without limitation. Depending on the specific radiation dose which is applied in step (d), the γ-sterilization is conducted for a period ranging from 2 to 10 hours, 3 to 8 hours, or 4 to 6 hours, e.g. 5 hours, without being limited thereto.

The diatomaceous earth composition obtained in step (d) of the above-defined method has a low endotoxin content, i.e. an endotoxin content of equal to or less than 0.5 EU/mL, preferably equal to or less than 0.2 EU/mL, and more preferably equal to or less than 0.1 EU/mL, which may be evaluated with the LAL test, as described above. After completion of the γ-sterilization in step (d), the diatomaceous earth composition may be stored at room temperature, i.e. further cooling is not required.

In step (e) of the method as defined above, the packaging which seals the agglomerated mixture of calcined diatomaceous earth particles and water is optionally removed from the diatomaceous earth composition which has been obtained in step (d). Preferably, the packaging is not removed until immediately before use.

In another aspect, the present invention relates to the use of the above-defined diatomaceous earth composition as a precoat agent for the precoat filtration in biopharmaceutical applications, and specifically relates to the use thereof for the precoat filtration of eukaryotic and/or prokaryotic cells in an aqueous medium.

In the biopharmaceutical process, when using diatomaceous earth as a precoat agent for the precoat filtration, it is particularly important to ensure a low endotoxin content along with a dust-free application of the diatomaceous earth. These requirements are fulfilled when using the diatomaceous earth composition according to the present invention.

The Figures show:

EXAMPLES

The present invention will be further illustrated by the way of Examples. However, the present invention is not to be construed as being limited to the following Examples.

Diatomaceous earth compositions comprising agglomerated mixtures of calcined diatomaceous earth particles (Celpure® C300, Advanced Minerals) and water in different mass ratios, sealed with a packaging, were unpacked and poured into a beaker. Then, the release of dust particles was determined over a period of one minute by means of a dust particle measurement instrument (MET ONE 3400, Hach).

Herein, the calcined diatomaceous earth particles had particles sizes of 10, 5, 3, 2, 1, and 0.5 μm, and the water had an endotoxin content of less than 0.05 EU/mL. The packaging used herein was a four-layered laminate comprising layers of PE (75 μm), OPA (12 μm), ALU (12 μm), and PET (12 μm).

Figure 1:
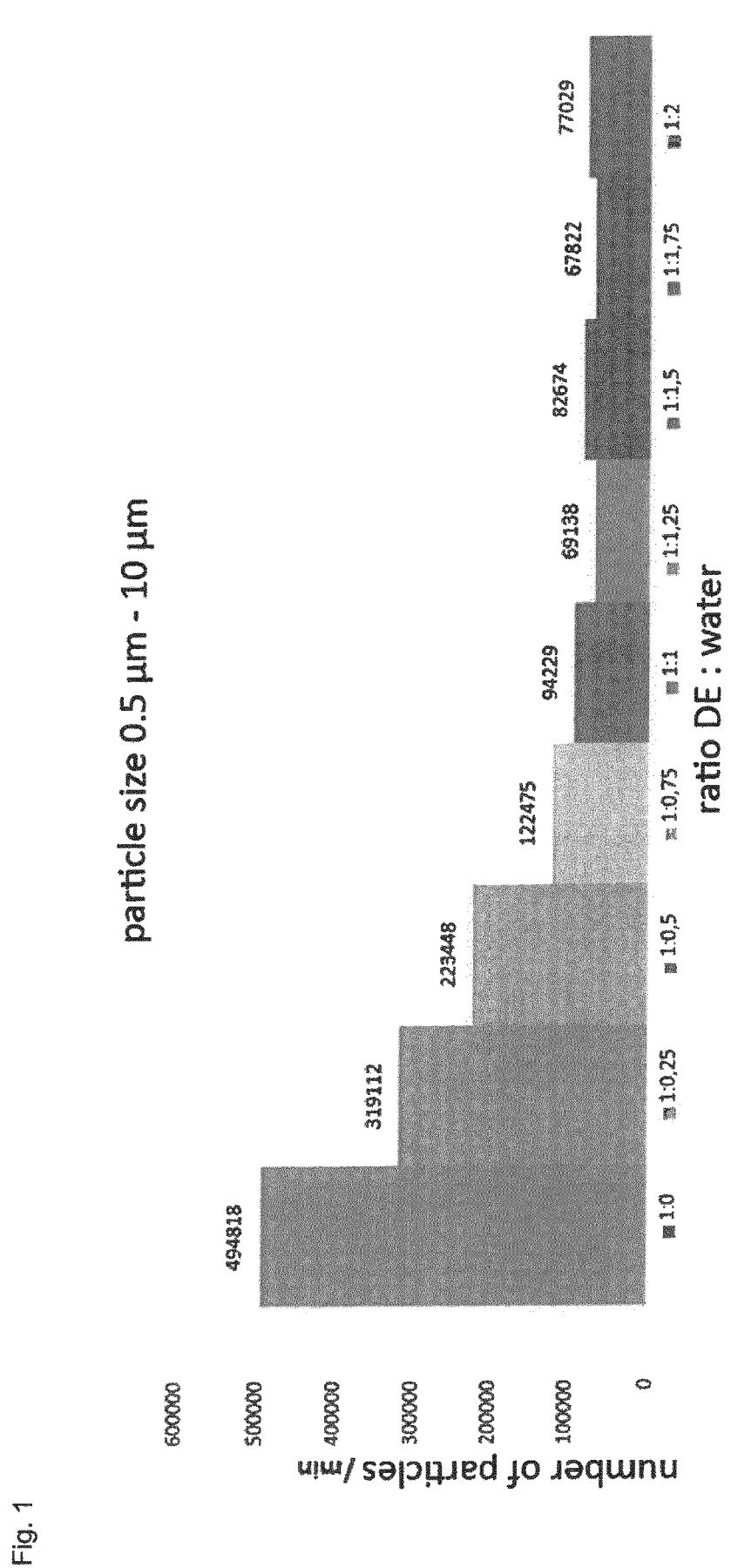
FIG. 1 shows the particle count rate (number of particles/min) as measured for different mass ratios of calcined diatomaceous earth particles and water.
Figure 2:
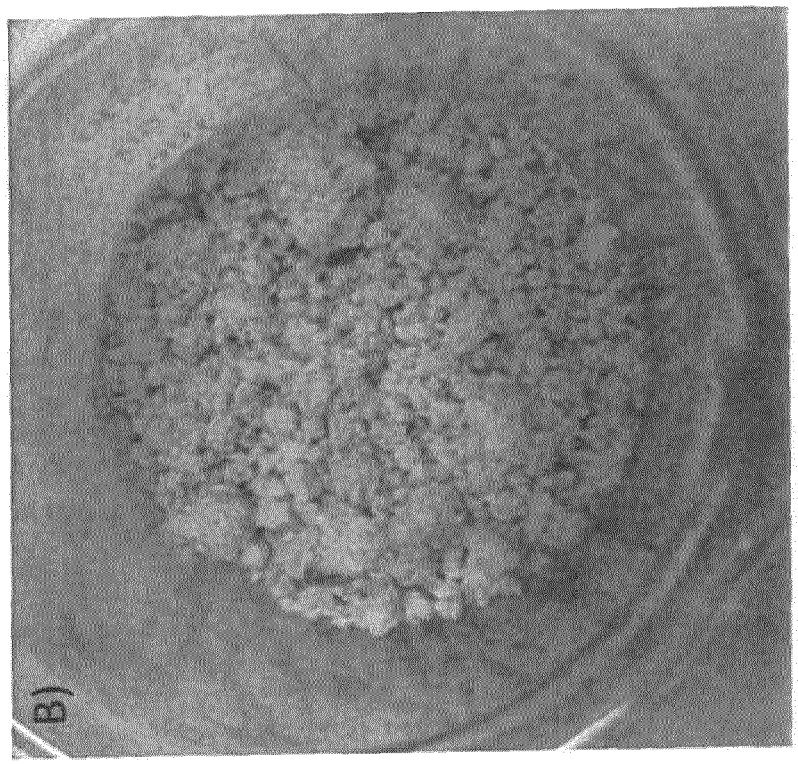
FIG. 2 shows photographic images of dry diatomaceous earth (FIG. 2A) and of a diatomaceous earth composition according to the present invention, having a mass ratio of calcined diatomaceous earth particles and water of 1:1.25, i.e. which contains the calcined diatomaceous earth particles in an amount of 44.4 mass %, and which contains water in an amount of 55.6 mass % (FIG. 2B).
Figure 2:

Unexpectedly, mixing one part of calcined diatomaceous earth particles and 1.25 parts of water led to a diatomaceous earth composition, wherein the release of dust particles is reduced by more than 85% compared to dry diatomaceous earth, as can be deduced from the respective particle count rates (number of particles/min) in FIG. 1. Surprisingly, as can be taken from FIG. 2, when comparing the diatomaceous earth composition having a mass ratio of calcined diatomaceous earth particles and water of 1:1.25 with the dry diatomaceous earth, no visible difference could be observed.

The diatomaceous earth composition according to the present invention, having a low endotoxin content, shows a reduced release of dust particles, while still exhibiting excellent free-flowing characteristics. As such, it is particularly suitable as a precoat agent for the precoat filtration in biopharmaceutical applications, in particular for the precoat filtration of eukaryotic and prokaryotic cells in an aqueous medium. Advantageously, the diatomaceous earth composition according to the present invention allows for an easy handling and minimizes the risk of inhaling dust particles.

The invention claimed is:

1. A method for producing a diatomaceous earth composition with a low endotoxin content, comprising the following steps:
   (a) providing calcined diatomaceous earth particles;
   (b) mixing the calcined diatomaceous earth particles with water in a mass ratio of 1:1.0 to 1:2.0, thereby obtaining an agglomerated mixture of calcined diatomaceous earth particles and water;
   (c) sealing the agglomerated mixture of calcined diatomaceous earth particles and water obtained in step (b) in a water-impermeable and γ-sterilizable packaging, thereby obtaining a sealed agglomerated mixture of calcined diatomaceous earth particles and water;
   (d) sterilizing the sealed agglomerated mixture of calcined diatomaceous earth particles and water obtained in step (c) by exposure to γ-radiation, thereby obtaining a diatomaceous earth composition with an endotoxin content of equal to or less than 0.5 EU/mL; and
   (e) optionally removing the packaging from the diatomaceous earth composition obtained in step (d).

2. The method according to claim 1, wherein the mass ratio of the calcined diatomaceous earth particles and water provided in step (a) is in the range of 1:1.1 to 1:1.7.

3. The method according to claim 2, wherein the mass ratio of the calcined diatomaceous earth particles and water provided in step (a) is in the range of 1:1.2 to 1:1.4.

4. The method according to claim 1, wherein the average particle size of the calcined diatomaceous earth particles provided in step (a) is in the range of 0.5 μm to 10 μm.

5. The method according to claim 1, wherein the calcined diatomaceous earth particles and water are mixed in step (b) by spray-wetting.

6. The method according to claim 1, wherein the water-impermeable and γ-sterilizable packaging for sealing the agglomerated mixture of calcined diatomaceous earth particles and water in step (c) is composed of a four-layered laminate comprising the following layers (i) to (iv) from the inside to the outside of the packaging:
   (i) a layer of polyethylene or polypropylene having a thickness in the range of 30 to 150 μm;
   (ii) a layer of polyethylene terephthalate or oriented polyamide having a thickness in the range of 5 μm to 20 μm;
   (iii) a layer of aluminum having a thickness in the range of 5 μm to 20 μm; and
   (iv) a layer of polyethylene terephthalate having a thickness in the range of 5 μm to 20 μm.

7. The method according of claim 1, wherein the γ-radiation for sterilizing the sealed agglomerated mixture of calcined diatomaceous earth particles and water in step (d) has a dose in the range of 25 kGy to 100 kGy.

* * * * *